United States Patent
Hayashi

(10) Patent No.: US 11,873,359 B2
(45) Date of Patent: Jan. 16, 2024

(54) PHOTOCURABLE COMPOSITION, THREE-DIMENSIONAL MOLDED PRODUCT, AND DENTAL PRODUCT

(71) Applicant: MITSUI CHEMICALS, INC., Tokyo (JP)

(72) Inventor: Takaaki Hayashi, Funabashi (JP)

(73) Assignee: MITSUI CHEMICALS, INC., Tokyo (JP)

(*) Notice: Subject to any disclaimer, the term of this patent is extended or adjusted under 35 U.S.C. 154(b) by 0 days.

(21) Appl. No.: 17/793,739

(22) PCT Filed: Jan. 8, 2021

(86) PCT No.: PCT/JP2021/000515
§ 371 (c)(1),
(2) Date: Jul. 19, 2022

(87) PCT Pub. No.: WO2021/149520
PCT Pub. Date: Jul. 29, 2021

(65) Prior Publication Data
US 2023/0091499 A1    Mar. 23, 2023

(30) Foreign Application Priority Data

Jan. 22, 2020   (JP) .................. 2020-008136

(51) Int. Cl.
| | |
|---|---|
| C08F 2/46 | (2006.01) |
| C08F 2/50 | (2006.01) |
| C08G 61/04 | (2006.01) |
| C08F 222/20 | (2006.01) |
| B33Y 70/00 | (2020.01) |
| A61K 6/887 | (2020.01) |
| A61K 6/62 | (2020.01) |
| C08K 5/00 | (2006.01) |

(52) U.S. Cl.
CPC ............. *C08F 222/20* (2013.01); *A61K 6/62* (2020.01); *A61K 6/887* (2020.01); *B33Y 70/00* (2014.12); *C08K 5/0041* (2013.01)

(58) Field of Classification Search
CPC . C08F 2/50; C08F 2/48; C08F 222/20; B33Y 70/00; B33Y 80/00; A61K 6/16; A61K 6/62; A61K 6/887; C08K 5/0041; C08L 33/08; C08L 33/10
USPC ....... 522/174, 173, 1, 189, 184, 6, 71; 520/1
See application file for complete search history.

(56) References Cited

U.S. PATENT DOCUMENTS

| | | |
|---|---|---|
| 8,993,650 B2 | 3/2015 | Uchida et al. |
| 2002/0127345 A1 | 9/2002 | Rheinberger et al. |
| 2010/0015578 A1 | 1/2010 | Falsafi et al. |
| 2014/0131908 A1 | 5/2014 | Sun et al. |
| 2019/0201171 A1 | 7/2019 | Raia et al. |

FOREIGN PATENT DOCUMENTS

| | | |
|---|---|---|
| CN | 108459468 * | 8/2018 |
| CN | 108714109 A | 10/2018 |
| JP | H08300492 A | 11/1996 |
| JP | 2005331695 A | 12/2005 |
| JP | 2006-348210 A | 12/2006 |
| JP | 2006348214 A | 12/2006 |
| JP | 4160311 B2 | 10/2008 |
| JP | 2010188610 A | 9/2010 |
| JP | 2016505525 A | 2/2016 |
| JP | 2016077887 A | 5/2016 |
| JP | 2019026594 A | 2/2019 |
| JP | 2019528197 A | 10/2019 |
| WO | 2018234898 A1 | 12/2018 |

OTHER PUBLICATIONS

Kawanishi, CN 108459468 Machine Translation, Aug. 28, 2018 (Year: 2018).*

* cited by examiner

*Primary Examiner* — Jessica Whiteley
(74) *Attorney, Agent, or Firm* — BUCHANAN INGERSOLL & ROONEY PC

(57) ABSTRACT

A photocurable composition includes a photopolymerizable component and a photopolymerization initiator, in which a diluted solution (D1) obtained by diluting the photocurable composition with ethanol such that the content of ethanol is 99% by mass would satisfy the following Condition (X): the transmittance at at least one wavelength within the wavelength range of from 365 nm to 405 nm, measured at an optical path length of 1 cm, is from 1.0% to 70.0%.

16 Claims, 1 Drawing Sheet

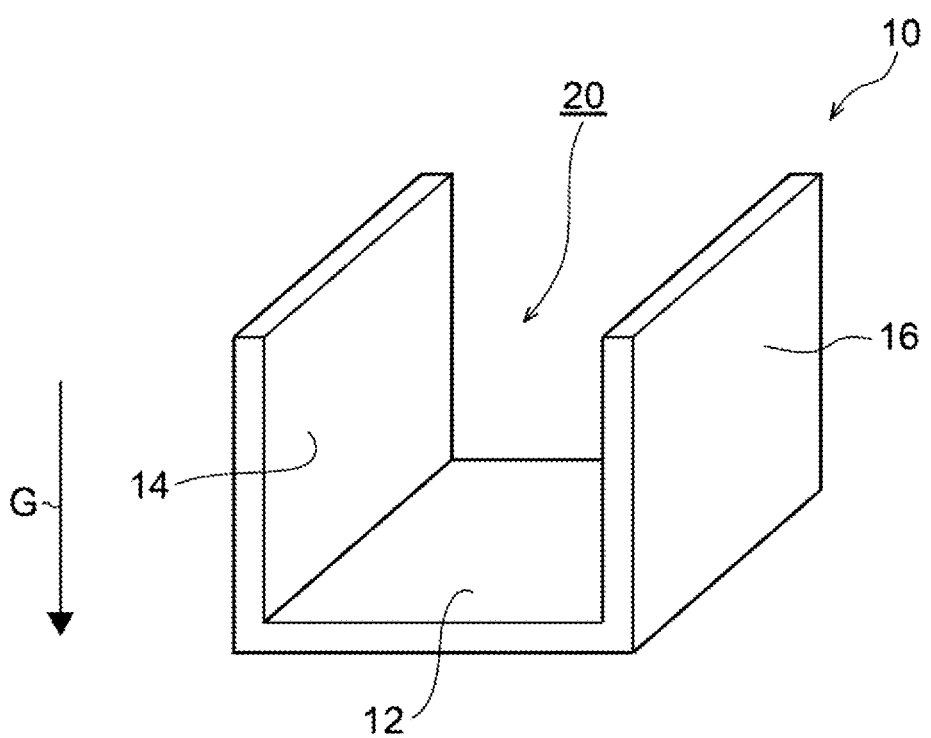

PHOTOCURABLE COMPOSITION, THREE-DIMENSIONAL MOLDED PRODUCT, AND DENTAL PRODUCT

TECHNICAL FIELD

The present disclosure relates to a photocurable composition, a three-dimensional molded product, and a dental product.

BACKGROUND ART

In recent years, studies on dental products, such as dental prosthetics and instruments used in the oral cavity, are being conducted. For example, from the viewpoint of efficiency of molding these dental products, a method of producing three-dimensional molded products such as dental products by optical molding using a 3D printer is known (see, for example, Patent Document 1).
Patent Document 1: Japanese Patent No. 4160311

SUMMARY OF INVENTION

Problem to be Solved by Invention

However, when producing a three-dimensional molded product by optical molding using a photocurable composition, a desired molding accuracy is not obtained in some cases. For example, there are cases in which the thickness of a part of a three-dimensional molded product becomes thicker than a desired thickness in the light travelling direction during optical molding (i.e., cases in which thickness accuracy is insufficient).

Therefore, there is a need for photocurable compositions that can produce a three-dimensional molded product with excellent molding accuracy.

An object of one aspect of the present disclosure is to provide a photocurable composition from which a three-dimensional molded product can be obtained with excellent molding accuracy, a three-dimensional molded product obtained from this photocurable composition, and a dental product.

Means for Solving the Problem

Means for solving the foregoing problem include the following aspects.

<1> A photocurable composition including a photopolymerizable component and a photopolymerization initiator, wherein
a diluted solution (D1) obtained by diluting the photocurable composition with ethanol in such a manner that the content of ethanol is 99% by mass would satisfy the following Condition (X),
Condition (X): The transmittance at at least one wavelength within the wavelength range of from 365 nm to 405 nm, measured at an optical path length of 1 cm, is from 1.0% to 70.0%.
<2> The photocurable composition according to <1>, wherein the diluted solution (D1) would satisfy at least one of the following Condition (1) or Condition (2),
Condition (1): The transmittance at a wavelength of 405 nm, measured at an optical path length of 1 cm, is from 1.0% to 70.0%, or
Condition (2): The transmittance at a wavelength of 385 nm, measured at an optical path length of 1 cm, is from 1.0% to 70.0%.
<3> The photocurable composition according to <2>, further including a colorant compound.
<4> The photocurable composition according to <3>, wherein
when the diluted solution (D1) satisfies the Condition (1), the sum of the values (A) defined in the following Formula (a) for respective colorant compounds contained in the photocurable composition is from 0.01 to 3.00, and
when the diluted solution (D1) satisfies the Condition (2), the sum of the values (B) defined in the following formula (b) for respective colorant compounds contained in the photocurable composition is from 0.01 to 3.00, $$\text{value}(A) = (x_1/y_1) \times 100 \quad \text{Formula (a)}$$

$$\text{value}(B) = (x_2/y_2) \times 100 \quad \text{Formula (b)}$$

wherein, in Formula (a), $x_1$ represents the content of a colorant compound in parts by mass with respect to 100 parts by mass of the photopolymerizable component contained in the photocurable composition, and $y_1$ represents the transmittance (%) at a wavelength of 405 nm measured at an optical path length of 0.5 cm for a diluted solution (D2) obtained by dilution with ethanol such that the content of the colorant compound is 0.01% by mass, and
wherein, in Formula (b), $x_2$ represents the content of the colorant compound in parts by mass with respect to 100 parts by mass of the photopolymerizable component contained in the photocurable composition, and $y_2$ represents the transmittance (%) at a wavelength of 385 nm measured at an optical path length of 0.5 cm for a diluted solution (D2) obtained by dilution with ethanol such that the content of the colorant compound is 0.01% by mass.
<5> The photocurable composition according to <3> or <4>, wherein
when the diluted solution (D1) satisfies the Condition (1), each colorant compound contained in the photocurable composition satisfies the following Condition (1-1), and
when the diluted solution (D1) satisfies the Condition (2), each colorant compound contained in the photocurable composition satisfies the following Condition (2-1),
Condition (1-1): The transmittance at a wavelength of 405 nm, measured at an optical path length of 0.5 cm for the diluted solution (D2) obtained by dilution with ethanol such that the content of a colorant compound is 0.01% by mass, is from 0.1% to 80.0%,
Condition (2-1) . . . The transmittance at a wavelength of 385 nm, measured at an optical path length of 0.5 cm for the diluted solution (D2) obtained by dilution with ethanol such that the content of the colorant compound is 0.01% by mass, is from 0.1% to 80.0%.
<6> The photocurable composition according to any one of <3> to <5>, wherein the colorant compound includes at least one of a dye or a pigment.
<7> The photocurable composition according to any one of <1> to <6>, wherein the photopolymerizable component includes a (meth)acrylic monomer.
<8> The photocurable composition according to <7>, wherein
the (meth)acrylic monomer includes at least one of a monofunctional (meth)acrylic monomer or a bifunctional (meth)acrylic monomer, and
the total amount of the bifunctional (meth)acrylic monomer and the monofunctional (meth)acrylic monomer with respect to the total amount of the (meth)acrylic monomer is 90% by mass or more.

<9> The photocurable composition according to <7> or <8>, wherein the (meth)acrylic monomer includes a bifunctional (meth)acrylic monomer.
<10> The photocurable composition according to any one of <1> to <9>, wherein the photocurable composition does not include any inorganic filler or, in a case in which the photocurable composition includes an inorganic filler, the content of the inorganic filler with respect to the total amount of the photocurable composition is 10% by mass or less.
<11> The photocurable composition according to any one of <1> to <10>, wherein the viscosity of the photocurable composition measured by an E-type viscometer under conditions of 25° C. and 50 rpm is from 5 mPa·s to 6,000 mPa·s.
<12> The photocurable composition according to any one of <1> to <11>, which is a photocurable composition for optical molding.
<13> The photocurable composition according to any one of <1> to <12>, which is used for producing a dental product.
<14> A three-dimensional molded product that is a cured product of the photocurable composition according to any one of <1> to <13>.
<15> The three-dimensional molded product according to <14>, including at least one of a recess portion or a space.
<16> A dental product including the three-dimensional molded product according to <14> or <15>.

Advantageous Effects of Invention

According to one aspect of the present disclosure, a photocurable composition from which a three-dimensional molded product can be obtained with excellent molding accuracy, a three-dimensional molded product obtained from this photocurable composition, and a dental product are provided.

BRIEF DESCRIPTION OF DRAWING

FIG. 1 is a schematic perspective view of one example of a three-dimensional molded product in the present disclosure.

DESCRIPTION OF EMBODIMENTS

In the present disclosure, numerical ranges expressed using "from A to B" means a range including numerical values A and B as a lower limit value and an upper limit value.

The term "step" in the present disclosure encompasses not only an independent step but also a step that cannot be clearly distinguished from another step as long as the desired object of the step of interest is achieved.

In the present disclosure, when there are plural substances corresponding to a particular component in the composition, the amount of the component included in the composition means the total amount of the plural substances present in the composition, unless otherwise specified.

In numerical ranges described stepwisely in the present disclosure, the upper limit value or lower limit value of one numerical range may be replaced by the upper limit value or lower limit value of another numerical range in the stepwise description. In a numerical range described in the present disclosure, the upper limit value or lower limit value of the numerical range may be replaced by a value described in Examples.

The term "light" in the present disclosure means a concept that encompasses an active energy radiation such as an ultraviolet light or a visible light.

As used herein, "(meth)acrylic monomer" means an acrylic monomer or a methacrylic monomer, "(meth)acryloyl group" means an acryloyl group or a methacryloyl group, "(meth)acrylate" means an acrylate or a methacrylate, (meth)acrylic acid" means acrylic acid or methacrylic acid, and "(meth)acrylonitrile" means acrylonitrile or methacrylonitrile.

[Photocurable Composition]

The photocurable composition of the present disclosure is a photocurable composition including a photopolymerizable component and a photopolymerization initiator, wherein
a diluted solution (D1) obtained by diluting the photocurable composition with ethanol such that the content of ethanol is 99% by mass would satisfy the following Condition (X).

Condition (X) . . . The transmittance at at least one wavelength within the wavelength range of from 365 nm to 405 nm, measured at an optical path length of 1 cm, is from 1.0% to 70.0%.

Conventionally, when producing a three-dimensional molded product by optical molding using a photocurable composition, there have been cases in which a desired molding accuracy is not obtained. For example, there have been cases in which the thickness of a part of a three-dimensional molded product becomes thicker than a desired thickness in the light travelling direction during optical molding (i.e., cases in which thickness accuracy is insufficient).

In this regard, according to the photocurable composition of the present disclosure, a three-dimensional molded product can be obtained with excellent molding accuracy (for example, excellent thickness accuracy) by satisfying the above-described Condition (X).

Hereinafter, an example of the above-described conventional problem and an example of an effect according to the photocurable composition of the present disclosure will be described.

As a method of optical molding, optical molding according to a liquid bath method (in other words, optical molding using a liquid bath) is known.

In the optical molding according to a liquid bath method, a portion of a photocurable composition included in a liquid bath (in other words, an uncured photocurable composition in the liquid state, the same applies hereinafter) is cured by light irradiation to form a cured layer, and this operation is repeated to stack cured layers, whereby a three-dimensional molded product is obtained. The optical molding according to a liquid bath method differs from optical molding according to an inkjet method in that a liquid bath is used.

Optical molding according to a liquid bath method is broadly classified into optical molding according to the DLP (Digital Light Processing) method and optical molding according to the SLA (Stereolithography) method. In the DLP method, a photocurable composition in a liquid bath is irradiated with planar light. In the SLA method, a photocurable composition in a liquid bath is irradiated with a laser beam in a scanning manner.

In one example of the optical molding according to the DLP method, for example, a 3D printer (for example, CARA PRINT 4.0 manufactured by Kulzer, MAX UV manufactured by Asiga, or the like) is used which is provided with:
a build table that is movable in the vertical direction;
a tray (i.e., a liquid bath) that is arranged below the build table (in the direction of gravity; the same applies hereinafter), and that includes an optically transparent portion, and that contains a photocurable composition; and a light source (for example, an LED light source) that is arranged below the tray, and that is configured to irradiate the photocurable composition in the tray with a planar light through the optically transparent portion of the tray.

In this example, first, a gap corresponding to one layer is provided between the build table and the tray, and this gap is filled with a photocurable composition. Next, the photocurable composition filled into the gap is irradiated with a planar light from below through the optically transparent portion of the tray, thereby curing a region irradiated with the light, to form a cured layer as the first layer. Next, the gap between the build table and the tray is widened by a distance corresponding to the next layer, and the generated space is filled with the photocurable composition. Next, the photocurable composition filled into the space is irradiated with light in the same manner as that in the curing of the first layer, to form a cured layer as the second layer. By repeating the operations described above, cured layers are stacked, whereby a three-dimensional molded product is produced.

FIG. 1 is a schematic perspective view of one example of a three-dimensional molded product (three-dimensional molded product 10) in the present disclosure.

As illustrated in FIG. 1, the three-dimensional molded product 10 includes a bottom face portion 12 and a pair of opposing side face portions 14 and 16. The pair of side face portions 14 and 16 are approximately perpendicular to the bottom face portion 12. The pair of side face portions 14 and 16 and the bottom face portion 12 form a recess portion 20.

The gravity direction G in FIG. 1 means the gravity direction during the production stage of the three-dimensional molded product 10. The travelling direction of light in the production stage of the three-dimensional molded product 10 is a direction opposite to the gravity direction G.

When a three-dimensional molded product 10 is produced by optical molding according to the DLP method, there is a case in which cured layers are stacked such that, for example, a pair of side face portions 14 and 16 are formed sequentially from the upper side (a side located upstream in the gravity direction G) to the lower side (a side located downstream in the gravity direction G), and, lastly, the bottom face portion 12 is formed. When the forming of the bottom face portion 12 is completed, the entire three-dimensional molded product 10 is arranged between the build table and the tray, and the top faces of the pair of side face portions 14 and 16 are in contact with the build table.

In the stage of forming the bottom face portion 12, only a desired thickness portion of the photocurable composition provided in a gap between the build table and the tray is cured to form one cured layer, and this operation is repeated to stack cured layers, whereby the bottom face portion 12 is formed. Specifically, at the stage of forming a cured layer for forming the bottom face portion 12, although the photocurable composition is also present in the region corresponding to the recess portion 20, the photocurable composition in the region corresponding to the recess portion 20 is not cured, and only the photocurable composition in the region corresponding to the cured layer for forming the bottom face portion 12 is cured in a layer shape.

Here, during forming of the bottom face portion 12 in the case of using a conventional photocurable composition, there are cases in which one cured layer becomes too thick as compared to a desired thickness, and, as a result, the thickness of the bottom face portion 12 formed by stacking cured layers becomes excessively large as compared to a desired thickness (i.e., a set value). It should be noted that the thickness mentioned here is the thickness with respect to the light traveling direction. It is conceivable that the reason why one cured layer becomes excessively thick as compared to a desired thickness is that the photocurable composition has an excessively high optical transparency, which causes not only curing of a portion of the photocurable composition corresponding to the thickness required to form the cured layer, but also curing of a portion of the photocurable composition that should not be cured (i.e., a region corresponding to the recess portion 20).

Further, in the case of using a conventional photocurable composition, when the irradiation dose of light is reduced to adjust one cured layer to a desired thickness, the curing becomes insufficient in some cases, and molding defects are caused thereby in some cases.

With respect to the above-described problem, when the photocurable composition of the present disclosure is used, a phenomenon in which the thickness of the bottom face portion 12 formed is too thick can be suppressed. In other words, the thickness accuracy of the bottom face portion 12 formed can be improved.

The reason that such an effect is achieved is considered to be that insufficiency and excessiveness of the optical transparency of the photocurable composition are suppressed due to the diluted solution (D1) of the photocurable composition of the present disclosure satisfying Condition (X). Suppression of insufficiency of optical transparency of the photocurable composition suppresses insufficiency of curing, thereby suppressing molding defects. Suppression of excessiveness of optical transparency of the photocurable composition suppresses excessiveness of the thickness of the cured layer.

The fact that the diluted solution (D1) of the photocurable composition of the present disclosure would satisfy Condition (X) means that the transmittance of the photocurable composition of the present disclosure at at least one wavelength included within the wavelength range of from 365 nm to 405 nm is within a specific range without excessiveness or insufficiency. Here, wavelengths within the wavelength range of from 365 nm to 405 nm (for example, a wavelength of 365 nm or a wavelength of 405 nm) are typical light wavelengths for 3D printers.

In order to strictly specify the transmittance range of a photocurable composition, the present disclosure specifies the transmittance of the diluted solution (D1) of the photocurable composition, rather than the transmittance of the photocurable composition itself.

Here, the diluted solution (D1) is a diluted solution obtained by diluting the photocurable composition of the present disclosure with ethanol such that the ethanol content is 99% by mass.

The above-described problem of thickness accuracy of the bottom face portion 12 in the three-dimensional molded product 10 is not limited to the bottom face portion 12 in the three-dimensional molded product 10, but can occur in a portion of any three-dimensional molded product having at least one of a recess portion or a space (for example, a dental product), which portion has a thickness direction that is the same as the light traveling direction (i.e., the vertical direction).

Here, the concept of a recess portion encompasses a recess portion formed by a bottom portion and at least a pair of side face portions (for example, a recess 20), a hole with a bottom end, and the like.

The concept of a space encompasses an interior space completely enclosed by walls of a three-dimensional molded product, a through hole, and the like.

<Applications>

Applications of the photocurable compositions of the present disclosure are not particularly restricted.

The photocurable composition of the present disclosure is preferably a photocurable composition for optical molding from the viewpoint of more effectively exhibiting an effect in terms of improving the molding accuracy of the three-dimensional molded product.

From the viewpoint of more effectively exhibiting an effect in terms of improving the thickness accuracy of the three-dimensional molded product (in particular, improving the thickness accuracy with respect to the light traveling direction during optical molding), the photocurable composition of the present disclosure is more preferably a photocurable composition for optical molding according to a liquid bath method (for example, the DLP or SLA method, preferably the DLP method), and is further preferably a photocurable composition for producing a three-dimensional molded product having at least one of a recess portion or a space by means of optical molding according to a liquid bath method.

The recess portion and the space are as described above.

From the viewpoint of more effectively exhibiting an effect in terms of improving the molding accuracy of the three-dimensional molded product, the photocurable composition of the present disclosure is preferably a photocurable composition for use in production of a dental product.

The dental product preferably includes a three-dimensional molded product having at least one of a recess portion or a space.

Examples of the dental product include a denture (in other words, an artificial tooth), a denture base, dental prosthetics, a medical device for use in the mouth, a dental model, and a vanishing casting model.

Examples of the dental prosthetics include an inlay, a crown, a bridge, a temporary crown, and a temporary bridge.

Examples of the medical device for use in the oral cavity include a mouthpiece, a mouthguard, an orthodontic appliance, a splint for occlusion, a tray for impression taking, and a surgical guide.

Examples of the dental model include a dental jaw model.

The photocurable composition of the present disclosure preferably satisfies at least one of Condition (1) or Condition (2) for the diluted solution (D1).

Condition (1): The transmittance at a wavelength of 405 nm, measured at an optical path length of 1 cm, is from 1.0% to 70.0%.

Condition (2): The transmittance at a wavelength of 385 nm, measured at an optical path length of 1 cm, is from 1.0% to 70.0%.

In the present disclosure, a photocurable composition according to an aspect in which the diluted solution (D1) satisfies Condition (1) may hereinafter be referred to as the photocurable composition according to a first embodiment, and a photocurable composition according to an aspect in which the diluted solution (D1) satisfies Condition (2) may be referred to as the photocurable composition according to a second embodiment.

That the diluted solution (D1) of the photocurable composition satisfies Condition (1) means that the transmittance of the photocurable composition at a wavelength of 405 nm is within a specific range without excessiveness or insufficiency, and that the diluted solution (D1) of the photocurable composition satisfies Condition (2) means that the transmittance of the photocurable composition at a wavelength of 385 nm is within a specific range without excessiveness or insufficiency.

As described above, wavelengths of 405 nm and 385 nm are typical light wavelengths for use in 3D printers.

For convenience of explanation, the photocurable composition according to the first embodiment and the photocurable composition according to the second embodiment are described separately below.

Note that the photocurable composition according to one of the first embodiment and the second embodiment may satisfy the requirement of the photocurable composition according to the other embodiment. For example, the photocurable composition according to the first embodiment may satisfy the requirement of the photocurable composition according to the second embodiment (in other words, the requirement that the diluted solution (D1) satisfy condition (2)).

The photocurable composition of the present disclosure is not limited to the following first embodiment and second embodiment. As described above, the photocurable composition of the present disclosure may be any composition as long as the composition includes a photopolymerizable component and a photopolymerization initiator, and the diluted solution (D1) thereof would satisfy Condition (X) (in other words, the condition that the transmittance at at least one wavelength within the wavelength range of from 365 nm to 405 nm, measured at an optical path length of 1 cm, is from 1.0% to 70.0%.), and there are no other particular restrictions.

The photocurable composition of the present disclosure may be a photocurable composition according to an embodiment other than the first embodiment and the second embodiment, or may be a photocurable composition that meets the requirement of the photocurable composition according to the first embodiment or the second embodiment as described below.

<Photocurable Composition According to First Embodiment>

The photocurable composition according to the first embodiment is a photocurable composition that includes a photopolymerizable component and a photopolymerization initiator, wherein a diluted solution (D1) obtained by diluting the photocurable composition with ethanol such that the content of ethanol is 99% by mass satisfies the following Condition (1).

Condition (1): The transmittance at a wavelength of 405 nm, measured at an optical path length of 1 cm, is from 1.0% to 70.0%.

Due to the photocurable composition according to the first embodiment allowing the diluted solution (D1) to satisfy Condition (1), insufficiency and excessiveness of transmittance of light at a wavelength of 405 nm through this photocurable composition are suppressed. This suppresses occurrence of insufficient curing of the photocurable composition according to the first embodiment (and resultant occurrence of molding defects) and occurrence of an excessive thickness (specifically, thickness in the light traveliong direction) of a cured region of the photocurable composition according to the first embodiment, and, as a result, allows a cured layer having a desired thickness to be obtained.

Specifically, due to the transmittance of the diluted solution (D1) at a wavelength of 405 nm being 1.0% or more, occurrence of insufficient curing of the photocurable composition according to the first embodiment is suppressed, and molding defects are suppressed thereby.

When the transmittance of the diluted solution (D1) at a wavelength of 405 nm is 70.0% or less, occurrence of an excessive thickness of the cured region of the photocurable composition according to the first embodiment is suppressed.

In Condition (1), the transmittance at a wavelength of 405 nm is preferably from 3.0% to 65.0%, and more preferably from 5.0% to 60.0%.

In the first embodiment, for example, adjustment such that the diluted solution (D1) of the photocurable composition satisfies Condition (1) can be made by adjusting the composition of the photocurable composition.

For example, when a photopolymerization initiator having a high transmittance at a wavelength of 405 nm is used as a photopolymerization initiator, adjustment such that the diluted solution (D1) satisfies Condition (1) can be made by adjusting the content of this photopolymerization initiator.

(Colorant Compound)

The photocurable composition according to the first embodiment preferably further includes a colorant compound. This makes it easier to make adjustment such that the diluted solution (D1) satisfies Condition (1).

In this case, only one colorant compound may be included in the photocurable composition according to the first embodiment, or two or more colorant compounds may be included in the photocurable composition according to the first embodiment.

The colorant compound preferably includes at least one of a dye or a pigment.

Examples of the Dye Include:

an anthraquinone dye (for example, quinizarin or alizanine);

a Sudan dye (such as Sudan II, Sudan III, or Sudan IV);

a Solvent Yellow dye (such as Solvent Yellow 2, Solvent Yellow 7, or Solvent Yellow a Solvent Green dye (such as Solvent Green 3 or Solvent Green 5);

a Solvent Orange dye (such as Solvent Orange 2);

a Solvent Blue dye (such as Solvent Blue 59);

a Basic Green dye (such as Basic Green 1);

an Acid Yellow dye (such as Acid Yellow 3); and an indophenol blue dye.

Among these dyes, a Sudan dye, a Solvent Yellow dye, or a Solvent Green dye is preferred.

The pigment may be an organic pigment (for example, phthalocyanine blue, phthalocyanine green, ultramarine blue, or a carminic acid pigment) or an inorganic pigment (for example titanium dioxide, carbon black, aluminum powder, caramel, iron oxide, ultramarine blue, iron blue, or chromium hydroxide).

As the colorant compound, a colorant compound that satisfies Condition (1-1) described below is preferred.

When the photocurable composition according to the first embodiment includes at least one colorant compound, the sum of the values (A) defined in the following formula (a) for the respective colorant compounds included in the photocurable composition is preferably from 0.01 to 3.00.

This makes it easier to make adjustment such that the diluted solution (D1) satisfies Condition (1).

The sum of the values (A) defined in the following Formula (a) for the respective colorant compounds included therein is more preferably from 0.04 to 3.00.

$$\text{value}(A) = (x_1/y_1) \times 100 \quad \text{Formula (a)}$$

wherein, in Formula (a), $x_1$ represents the content of a colorant compound in parts by mass with respect to 100 parts by mass of the photopolymerizable component contained in the photocurable composition, and $y_1$ represents the transmittance (%) at a wavelength of 405 nm measured at an optical path length of 0.5 cm for a diluted solution (D2) obtained by dilution with ethanol such that the content of the colorant compound is 0.01% by mass.

The technical meaning of the sum of values (A) in the first embodiment will be described below.

The technical meaning of the sum of values (B) in the second embodiment, described below, is also the same as the technical meaning of the sum of values (A) in the first embodiment, except for the wavelength.

The sum of values (A) is a value that correlates with the total amount of colorant compounds contained in the photocurable composition according to the first embodiment.

Note that in Formula (a), which defines the value (A), the value (A) is defined using $x_1$ and $y_1$, considering that the preferred content varies depending on the transmittance (%) at 405 nm wavelength of a colorant compound. For example, the content of a colorant compound having a low transmittance at a wavelength of 405 nm is preferablly low as compared to the content of a colorant compound having a high transmittance at a wavelength of 405 nm.

In Formula (a), in order to strictly specify the transmittance range of a colorant compound, the transmittance of the diluted solution (D2) of the colorant compound, rather than the transmittance of the colorant compound itself, is specified.

When the photocurable composition according to the first embodiment includes at least one colorant compound, each colorant compound contained in the photocurable composition preferably satisfies the following Condition (1-1).

This makes it easier to make adjustment such that the diluted solution (D1) satisfies Condition (1).

Condition (1-1) . . . The transmittance at a wavelength of 405 nm, measured at an optical path length of 0.5 cm, for the diluted solution (D2) obtained by diluting the colorant compound with ethanol such that the content of the colorant compound is 0.01% by mass, is from 0.1% to 80.0%.

In Condition (1-1), the transmittance at a wavelength of 405 nm for the diluted solution (D2) is preferably from 0.3% to 75.0%.

Also in Condition (1-1) in the first embodiment, in order to strictly specify the transmittance range of a colorant compound, the transmittance of the diluted solution (D2) of the colorant compound, rather than the transmittance of the colorant compound itself, is specified.

The same is true for Condition (2-1) in the second embodiment described below.

(Photopolymerizable Component)

The photocurable composition according to the first embodiment includes at least one photopolymerizable component.

Examples of the photopolymerizable component include a compound containing an ethylenic double bond.

Examples of the compound containing an ethylenic double bond include a (meth)acrylic monomer, styrene, a styrene derivative, and (meth)acrylonitrile.

As the photopolymerizable component, a photopolymerizable component described in paragraphs [0030] to [0059] of International Publication (WO) 2019/189652 may be used.

The photopolymerizable component preferably includes at least one (meth)acrylic monomer.

In this case, the total proportion of (meth)acrylic monomers with respect to the entire photopolymerizable component is preferably 80% by mass or more, more preferably 90% by mass, and still more preferably 95% by mass or more.

The (meth)acrylic monomer may be any monomer that contains one or more (meth)acryloyl groups in a molecule thereof, and there are no other particular restrictions.

The (meth)acrylic monomer may be a monofunctional (meth)acrylic monomer (i.e., a monomer containing one (meth)acryloyl group in a molecule thereof), a bifunctional (meth)acrylic monomer (i.e., a monomer containing two (meth)acryloyl groups in a molecule thereof), or a polyfunctional (meth)acrylic monomer (i.e., a monomer containing three or more (meth)acryloyl groups in a molecule thereof).

The (meth)acrylic monomer preferably contains, in a molecule thereof, at least one of an aromatic structure (such as a bisphenol A structure), an alicyclic structure, or a urethane bond.

The (meth)acrylic monomer in such a preferable aspect may further contain at least one of an ethyleneoxy group or a propyleneoxy group.

The molecular weight of the (meth)acrylic monomer is preferably 5,000 or less, more preferably 3,000 or less, still more preferably 2,000 or less, still more preferably 1,500 or less, still more preferably 1,000 or less, and still more preferably 800 or less.

The lower limit of the molecular weight of the (meth) acrylic monomer is not particularly restricted as long as the monomer contains one or more (meth)acryloyl groups in a molecule thereof. The lower limit of the molecular weight of (meth)acrylic monomer is, for example, 86, and preferably 100, more preferably 200, and still more preferably 300.

From the viewpoint of viscosity reduction of the photocurable composition according to the first embodiment, the (meth)acrylic monomer, which can be included in the photocurable composition according to the first embodiment, preferably includes at least one of a monofunctional (meth) acrylic monomer or a bifunctional (meth)acrylic monomer.

In this case, from the viewpoint of viscosity reduction of the photocurable composition according to the first embodiment, the total amount of bifunctional (meth)acrylic monomers and monofunctional (meth)acrylic monomers with respect to the total amount of (meth)acrylic monomers optionally included in the photocurable composition according to the first embodiment is preferably 60% by mass or more, more preferably 80% by mass or more, and still more preferably 90% by mass or more.

Specific examples of the monofunctional (meth)acrylic monomer include cyclohexyl (meth)acrylate, isobornyl (meth)acrylate, dicyclopentanyl (meth)acrylate, dicyclopentenyl (meth)acrylate, 4-tert-butylcyclohexyl (meth)acrylate, tetrahydrofurfuryl (meth)acrylate, (2-methyl-2-ethyl-1,3-dioxolan-4-yl)methyl (meth)acrylate, cyclic trimethylolpropaneformal (meth)acrylate, 4-(meth)acryloylmorpholine, lauryl (meth)acrylate, 4-hydroxybutyl (meth)acrylate, 2-hydroxyethyl (meth)acrylate, phenoxyethylene glycol (meth) acrylate, 2-dodecyl-1-hexadecanyl (meth)acrylate, 2-(meth) acryloyloxyethyl succinate, 2-[[(butylamino)carbonyl]oxy] ethyl (meth)acrylate, and 2-(2-ethoxyethoxy)ethyl (meth) acrylate.

Specific examples of the bifunctional (meth)acrylic monomer include ethylene glycol di(meth)acrylate, triethylene glycol di(meth)acrylate, glycerin di(meth)acrylate, 1,6-hexanediol di(meth)acrylate, ethoxylated bisphenol A di(meth)acrylate, dimethylol-tricyclodecane di(meth)acrylate, 1,9-nonanediol di(meth)acrylate, dioxane glycol di(meth)acrylate, diethylene glycol di(meth)acrylate, dipropylene glycol di(meth)acrylate, ethoxylated bisphenol A di(meth) acrylate, ethoxylated hydrogenated bisphenol A di(meth) acrylate, 2-hydroxy-3-acryloyloxypropyl (meth)acrylate, bis (2-(meth)acryloxyethyl) N,N'-1,9-nonylene biscarbamate (diurethane (meth)acrylate), polyethylene glycol di(meth) acrylate, and polypropylene glycol di(meth)acrylate.

From the viewpoint of further promoting curing of the photocurable composition and further improving the molding accuracy of the three-dimensional molded product, the (meth)acrylic monomer that can be included in the photocurable composition according to the first embodiment preferably includes a bifunctional (meth)acrylic monomer.

In this case, from the viewpoint of further promoting the curing of the photocurable composition and improving the molding accuracy of the molded product, the total amount of bifunctional (meth)acrylic monomers with respect to the total amount of (meth)acrylic monomers optionally included in the photocurable composition according to the first embodiment is preferably 60% by mass or more, more preferably 80% by mass or more, and still more preferably 90% by mass or more.

From the viewpoint of further promoting curing of a photocurable composition and further improving the molding accuracy of the molded product, the (meth)acrylic monomer that can be included in the photocurable composition according to the first embodiment more preferably includes:

Monomer M1, which is a bifunctional (meth)acrylic monomer containing, in a molecule thereof, at least one of an aromatic ring structure (for example, a bisphenol A structure) or an alicyclic structure; and Monomer M2, which is a bifunctional (meth)acrylic monomer containing a urethane bond in a molecule thereof.

In this case, the total amount of Monomer M1 and Monomer M2 relative to the total amount of (meth)acrylic monomers optionally included in the photocurable composition according to the first embodiment is preferably 60% by mass or more, more preferably 80% by mass or more, and still more preferably 90% by mass or more.

When the (meth)acrylic monomer optionally included in the photocurable composition according to the first embodiment includes Monomer M1 and Monomer M2, the content mass ratio of Monomer M1 to the total of Monomer M1 and Monomer M2 (i.e., the content mass ratio [Monomer M1/ (Monomer M1+Monomer M2)]) is preferably from 0.50 to less than 1.00, more preferably from 0.55 to 0.95, and still more preferably from 0.60 to 0.80.

Monomer M1 preferably further contains at least one of an ethyleneoxy group or a propyleneoxy group. As Monomer M1, a bifunctional (meth)acrylic monomer containing, in a molecule thereof, at least one of an ethyleneoxy group or a propyleneoxy group and a bisphenol A structure is particularly preferred.

Monomer M2 preferably further contains at least one of an ethyleneoxy group or a propyleneoxy group, and an alkylene group. As Monomer M2, a bifunctional (meth) acrylic monomer containing, in a molecule thereof, at least one of an ethyleneoxy group or a propyleneoxy group, a urethane bond, and an alkylene group is particularly preferred.

The amount of photopolymerizable component included in the photocurable composition according to the first embodiment is not particularly limited.

From the viewpoint of improving the molding accuracy of the three-dimensional molded product, the content of the photopolymerizable component with respect to 100 parts by mass of the photocurable composition is preferably 60 parts by mass or more, more preferably 80 parts by mass or more, and still more preferably 90 parts by mass or more.

(Photopolymerization Initiator)

The photocurable composition according to the first embodiment includes at least one photopolymerization initiator.

Examples of the photopolymerization initiator include an alkylphenone compound, an acylphosphine oxide compound, titanosen compound, an oxime ester compound, benzoin compound, an acetophenone compound, benzophenone compound, thioxanthone compound, an α-acyloxime ester compound, a phenylglyoxylate compound, a benzyl compound, an azo compound, a diphenyl sulfide compound, an iron-phthalocyanine compound, a benzoin ether compound, and an anthraquinone compound.

From the viewpoint of reactivity, the photopolymerization initiator preferably includes at least one selected from the group consisting of an alkylphenone compound and an acylphosphine oxide compound.

From the viewpoint of improving the molding accuracy of the three-dimensional molded product, the photopolymerization initiator preferably includes an acylphosphine oxide compound (for example 2,4,6-trimethylbenzoyl-diphenyl-phosphine oxide or bis(2,4,6-trimethylbenzoyl)phenylphosphine oxide), and more preferably includes 2,4,6-trimethyl-benzoyl-diphenyl-phosphine oxide.

The transmittance at a wavelength of 385 nm of the photopolymerization initiator included in the photocurable composition according to the first embodiment, measured at an optical path length of 1 cm, is preferably 80% or more, more preferably 82% or more, and still more preferably 84% or more.

When the above-described transmittance of the photopolymerization initiator is 80% or higher, an influence of the photopolymerization initiator on the light transmittance of the photocurable composition during photopolymerization can be further reduced.

From the viewpoint of further reducing an influence on the light transmittance of the photocurable composition during photopolymerization, the photopolymerization initiator is preferably a photopolymerization initiator of which light absorption peak in the wavelength region of 220 nm or more is positioned at a wavelength of 340 nm or less.

Examples of the photopolymerization initiator of which light absorption peak in the wavelength region of 220 nm or more is positioned at a wavelength of 340 nm or less include 2,4,6-trimethylbenzoyl-diphenyl-phosphine oxide, bis(2,4,6-trimethylbenzoyl) phenylphosphine oxide, 1-hydroxy-cyclohexylphenylketone, phenylglyoxylic acid methyl ester, 2,2-dimethoxy-1,2-diphenylethane-1-one, 2-hydroxy-2-methyl-1-phenyl-propane-1-one, 2-dimethylamino-2-(4-methyl-benzyl)-1-(4-morpholin-4-yl-phenyl)-butane-1-one, 1,2-octanedione, and 1-{4-(phenylthio)-, 2-(O-benzoyloxime)}.

The amount of the photopolymerization initiator contained in the photocurable composition according to the first embodiment, with respect to 100 parts by mass of the photopolymerizable component, is preferably from 0.1 parts by mass to 20 parts by mass, more preferably from 0.5 parts by mass to 10 parts by mass, and still more preferably from 1 part by mass to 5 parts by mass.

(Other Component)

The photocurable composition according to the first embodiment may, if necessary, include another component other than those mentioned above.

Examples of the other component include an inorganic filler, a modifier, a stabilizer, an antioxidant, and a solvent.

From the viewpoint of further improving the molding accuracy of the three-dimensional molded product, the photocurable composition according to the first embodiment preferably does not include an inorganic filler (for example, silica, barium borosilicate glass, or the like; the same applies hereinafter), or when the photocurable composition includes an inorganic filler, the content of the inorganic filler with respect to the total amount of the photocurable composition is preferably 10% by mass or less (more preferably 5% by mass or less, still more preferably 2% by mass or less, and still more preferably 1% by mass or less).

<Photocurable Composition According to Second Embodiment>

The photocurable composition according to the second embodiment is a photocurable composition that includes a photopolymerizable component and a photopolymerization initiator, wherein a diluted solution (D1) obtained by diluting the photocurable composition with ethanol such that the content of ethanol is 99% by mass satisfies the following Condition (2).

Condition (2): The transmittance at a wavelength of 385 nm, measured at an optical path length of 1 cm, is from 1.0% to 70.0%.

Due to the photocurable composition according to the second embodiment allowing the diluted solution (D1) to satisfy Condition (2), insufficiency or excessiveness of transmittance of light at a wavelength of 385 nm through this photocurable composition are suppressed. This suppresses occurrence of insufficient curing of the photocurable composition according to the second embodiment (and resultant occurrence of molding defects) and occurrence of an excessive thickness (specifically, thickness in the light traveling direction) of a cured region of the photocurable composition according to the second embodiment, and, as a result, allows a cured layer having a desired thickness to be obtained.

Specifically, due to the transmittance of the diluted solution (D1) at a wavelength of 385 nm being 1.0% or more, occurrence of insufficient curing of the photocurable composition according to the second embodiment is suppressed, and molding defects are suppressed thereby.

When the transmittance of the diluted solution (D1) at a wavelength of 385 nm is 70.0% or less, occurrence of an excessive thickness of the cured region of the photocurable composition according to the second embodiment is suppressed.

In Condition (2), the transmittance at a wavelength of 385 nm is preferably from 3.0% to 65.0%, and more preferably from 5.0% to 65.0%.

In the second embodiment, for example, adjustment such that the diluted solution (D1) of the photocurable composition satisfies Condition (2) can be made by adjusting the composition of the photocurable composition.

For example, when a photopolymerization initiator having a high transmittance at a wavelength of 385 nm is used as a photopolymerization initiator, adjustment such that the diluted solution (D1) satisfies Condition (2) can be made by adjusting the content of this photopolymerization initiator.

(Colorant Compound)

The photocurable composition according to the second embodiment preferably further includes a colorant compound. This makes it easier to make adjustment such that the diluted solution (D1) satisfies Condition (2).

In this case, only one colorant compound may be included in the photocurable composition according to the second embodiment, or two or more colorant compounds may be included in the photocurable composition according to the second embodiment.

The colorant compound in the second embodiment preferably includes at least one of a dye or a pigment.

The dye and the pigment that can be included in the photocurable composition according to the second embodiment are the same as the dye and the pigment that can be included in the photocurable composition according to the first embodiment, respectively.

Specific examples of colorant compounds that can be included in the photocurable composition according to the second embodiment are the same as those of colorant compounds that can be included in the photocurable composition according to the first embodiment.

As the colorant compound, a colorant compound that satisfies Condition (2-1) described below is preferred.

When the photocurable composition according to the second embodiment includes at least one colorant compound, the sum of the values (B) defined in the following formula (b) for the respective colorant compound included in the photocurable composition is preferably from 0.01 to 3.00.

This makes it easier to make adjustment such that the diluted solution (D1) satisfies Condition (2).

The sum of the values (B) defined in the following Formula (b) for the respective colorant compounds included therein is more preferably from 0.04 to 3.00.

$$\text{value}(B) = (x_2/y_2) \times 100 \quad \text{Formula (b)}$$

wherein, in Formula (b), $x_2$ represents the content of a colorant compound in parts by mass with respect to 100 parts by mass of the photopolymerizable component contained in the photocurable composition, and $y_2$ represents the transmittance (%) at a wavelength of 385 nm measured at an optical path length of 0.5 cm for a diluted solution (D2) obtained by dilution with ethanol such that the content of the colorant compound is 0.01% by mass.

When the photocurable composition according to the second embodiment includes at least one colorant compound, each colorant compound contained in the photocurable composition preferably satisfies the following Condition (2-1).

This makes it easier to make adjustment such that the diluted solution (D1) satisfies Condition (2).

Condition (2-1) . . . The transmittance at a wavelength of 385 nm, measured at an optical path length of 0.5 cm, for the diluted solution (D2) obtained by diluting the colorant compound with ethanol such that the content of a colorant compound is 0.01% by mass, is from 0.1% to 80.0%.

In Condition (2-1), the transmittance at a wavelength of 385 nm for the diluted solution (D2) is preferably from 0.3% to 80.0%.

(Photopolymerizable Component)

The photocurable composition according to the second embodiment includes at least one photopolymerizable component.

The photopolymerizable component and preferred aspects thereof in the second embodiment are the same as the above-described photopolymerizable component and preferred aspects thereof in the first embodiment. Accordingly, for the photopolymerizable component in the second embodiment, the description in the "photopolymerizable component" section in the first embodiment can be referred to, as appropriate.

(Photopolymerization Initiator)

The photocurable composition according to the second embodiment includes at least one photopolymerization initiator.

The photopolymerization initiator and preferred aspects thereof in the second embodiment are the same as the above-described photopolymerization initiator and preferred aspects thereof in the first embodiment. Accordingly, for the photopolymerization initiator in the second embodiment, the description in the "photopolymerization initiator" section in the first embodiment can be referred to, as appropriate.

In this regard, the transmittance at a wavelength of 405 nm of the photopolymerization initiator contained in the photocurable composition according to the second embodiment, measured at an optical path length of 1 cm, is preferably 80% or more, more preferably 83% or more, and still more preferably 85% or more.

(Other Component)

The photocurable composition according to the second embodiment may, if necessary, include another component other than those mentioned above.

Examples of the other component include an inorganic filler, a modifier, a stabilizer, an antioxidant, and a solvent.

From the viewpoint of further improving the molding accuracy of the three-dimensional molded product, the photocurable composition according to the second embodiment preferably does not include an inorganic filler (for example, glass fiber or the like; the same applies hereinafter.), or when the photocurable composition includes an inorganic filler, the content of the inorganic filler with respect to the total amount of the photocurable composition is preferably 10% by mass or less (more preferably 5% by mass or less, still more preferably 2% by mass or less, and still more preferably 1% by mass or less).

<Preferred Viscosity of Photocurable Composition>

The photocurable composition of the present disclosure (for example, each of the photocurable composition according to the first embodiment and the photocurable composition according to the second embodiment described above) preferably has a viscosity (hereinafter, also simply referred to as "viscosity") of from 5 mPa·s to 6,000 mPa·s, as measured under conditions of 25° C. and 50 rpm with an E-type viscometer.

Here, rpm means revolutions per minute.

When the viscosity is from 5 mPa·s to 6,000 mPa·s, the photocurable composition has excellent handleability when a three-dimensional molded product is produced by optical molding.

The viscosity is more preferably from 10 mPa·s to 5,000 mPa·s, still more preferably from 20 mPa·s to 4,000 mPa·s, still more preferably from 100 mPa·s to 3,000 mPa·s, still more preferably from 200 mPa·s to 2,000 mPa·s, and still more preferably from 400 mPa·s to 1,500 mPa·s.

[Three-Dimensional Molded Product]

The three-dimensional molded product of the present disclosure is a cured product of the photocurable composition of the present disclosure described above.

Therefore, the three-dimensional molded product of the present disclosure has excellent molding accuracy.

The three-dimensional molded product of the present disclosure is preferably a three-dimensional molded product having at least one of a recess portion or a space.

The recess portion and the space are each as described above.

[Dental Product]

The dental product of the present disclosure includes the three-dimensional molded product of the present disclosure (preferably, three-dimensional molded product having a recess portion or a space) as described above.

Therefore, the dental product of the present disclosure has excellent molding accuracy.

Specific examples of the dental product are as described above.

EXAMPLES

Examples of the present disclosure will be described below, but the present disclosure is not limited to the following Examples.

<Preparation of Photocurable Composition>

Photocurable compositions of Examples 1 to 30 and 101 to 120, and in Comparative Examples 1 to 4 and 101 to 107 were each prepared by mixing the materials indicated in Tables 1 to 5 below.

Here, Examples 1 to 30 and Comparative Examples 1 to 4 are examples and comparative examples of the photocurable composition according to the first embodiment, and Examples 101 to 120 and Comparative Examples 101 to 107 are examples and comparative examples of the photocurable composition according to the second embodiment.

The details of materials (photopolymerizable components, photopolymerization initiators, and colorant compounds) shown in Tables 1 to 5 below are as follows.

In Tables 1 to 5 below, the numerical values shown in the columns for the respective components in each of Examples and Comparative Examples indicate the parts by mass of the respective components with respect to 100 parts by mass of the total photopolymerizable components.

(Photopolymerizable Component)

ABE300: Ethoxylated bisphenol A diacrylate (Shin Nakamura Chemical Industry Co., Ltd.; having the structure shown below)

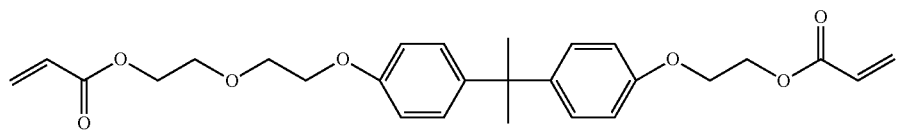 [SMILES: C=CC(=O)OCCOCCOc1ccc(C(C)(C)c2ccc(OCCOC(=O)C=C)cc2)cc1]

UDA: Urethane diacrylate (FUJIFILM Wako Pure Chemical Corporation; having the structure shown below)

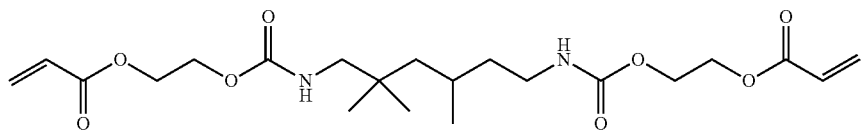 [SMILES: C=CC(=O)OCCOC(=O)NCCC(C)CC(C)(C)CNC(=O)OCCOC(=O)C=C]

SR540: Ethoxylated bisphenol A dimethacrylate (Sartomer Corporation; having the structure shown below)

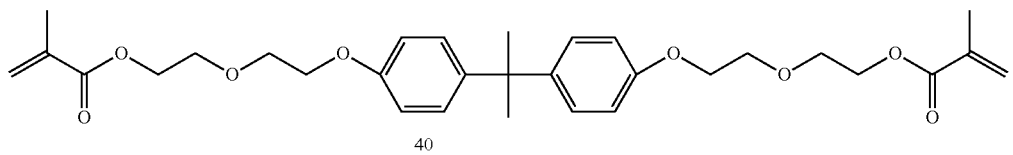

UDMA: urethane dimethacrylate (FUJIFILM Wako Pure Chemical Corporation; having the structure shown below)

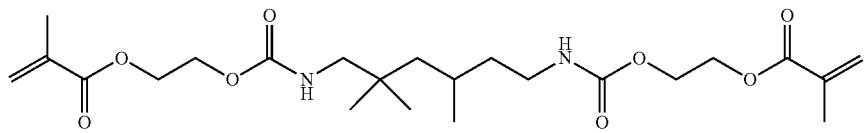 [SMILES: C=C(C)C(=O)OCCOC(=O)NCCC(C)CC(C)(C)CNC(=O)OCCOC(=O)C(=C)C]

(Photopolymerization Initiator)

TPO: Acylphosphine oxide compound (specifically, 2,4,6-trimethylbenzoyl-diphenyl-phosphine oxide) (OMNIRAD TPO H, IGM Resins B.V; having the structure shown below)

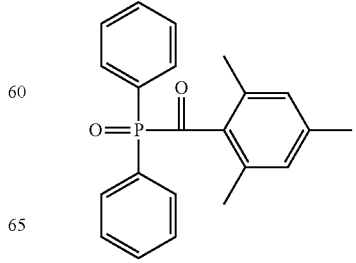

819: Acylphosphine oxide compound (specifically, bis(2,4,6-trimethylbenzoyl)phenylphosphine oxide) (OMNIRAD 819, IGM Resins B.V.; having the structure shown below)

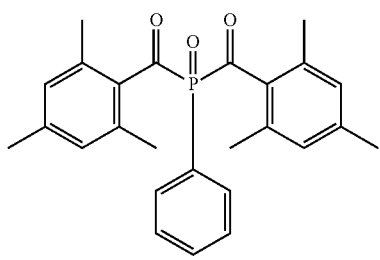

184: 1-hydroxy-cyclohexyl phenylketone (OMNIRAD 184, IGM Resins B.V.; having the structure shoen below)

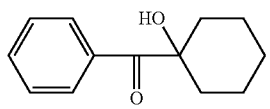 [SMILES: O=C(c1ccccc1)C1(O)CCCCC1]

MBF: Phenylglyoxylic acid methyl ester (OMNIRAD MDF, IGM Resins B.V.; having the structure shown below)

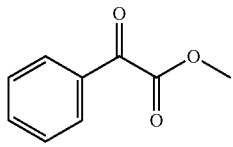

(Colorant Compound)

Quinizarin (Tokyo Chemical Industry Co., Ltd.; having the structure shown below)

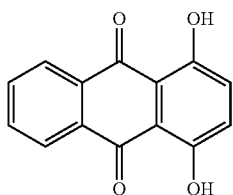 [SMILES: O=C1c2ccccc2C(=O)c2c(O)ccc(O)c21]

Alizarin (Tokyo Chemical Industry Co., Ltd.; having the structure shown below)

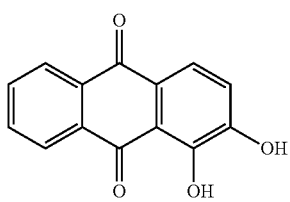 [SMILES: O=C1c2ccccc2C(=O)c2c1ccc(O)c2O]

Solvent Green 3 (Tokyo Chemical Industry Co., Ltd.; having the structure shown below)

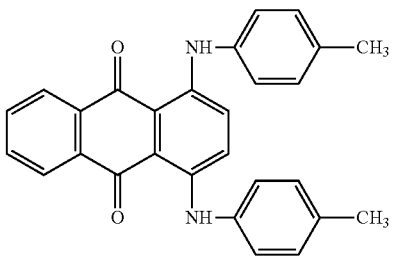 [SMILES: Cc1ccc(Nc2ccc(Nc3ccc(C)cc3)c3c2C(=O)c2ccccc2C3=O)cc1]

Sudan II (Tokyo Chemical Industry Co., Ltd.; having the structure shown below)

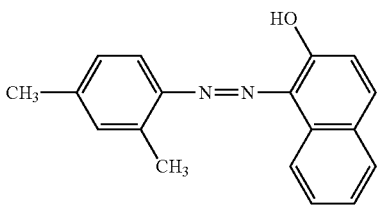 [SMILES: Cc1ccc(N=Nc2c(O)ccc3ccccc23)c(C)c1]

Sudan III (Tokyo Chemical Industry Co., Ltd.; having the structure shown below)

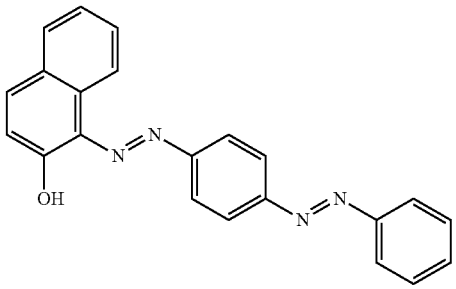 [SMILES: Oc1ccc2ccccc2c1/N=N/c1ccc(/N=N/c2ccccc2)cc1]

Sudan IV (Tokyo Chemical Industry Co., Ltd.; having the structure shown below)

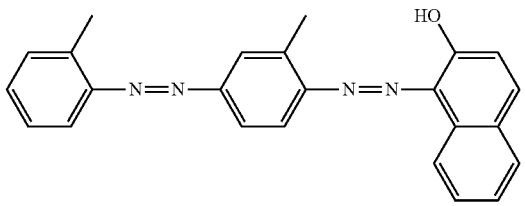 [SMILES: Cc1ccccc1N=Nc1ccc(N=Nc2c(O)ccc3ccccc23)c(C)c1]

Solvent Orange 2 (Tokyo Chemical Industry Co., Ltd.; having the structure shown below)

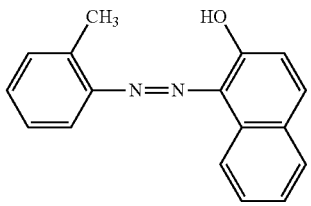 [SMILES: Cc1ccccc1N=Nc1c(O)ccc2ccccc12]

Solvent Yellow 2 (Tokyo Chemical Industry Co., Ltd.; having the structure shown below)

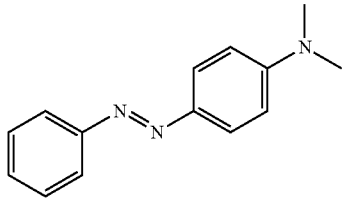 [SMILES: CN(C)c1ccc(/N=N/c2ccccc2)cc1]

Solvent Yellow 11 (Tokyo Chemical Industry Co., Ltd.; having the structure shown below)

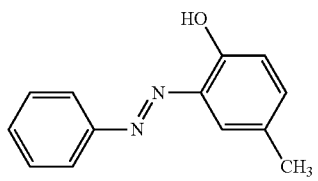 [SMILES: Cc1ccc(O)c(/N=N/c2ccccc2)c1]

Solvent Yellow 7 (Tokyo Chemical Industry Co., Ltd.; having the structure shown below)

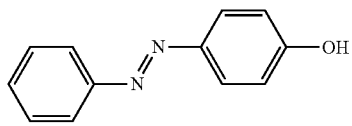 [SMILES: Oc1ccc(/N=N/c2ccccc2)cc1]

Basic Green 1 (Tokyo Chemical Industry Co., Ltd.; having the structure shown

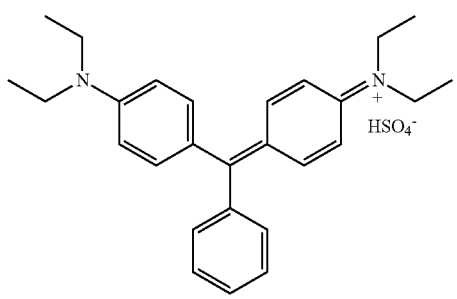

Acid Yellow 3 (Tokyo Chemical Industry Co., Ltd.; having the structure shown below)

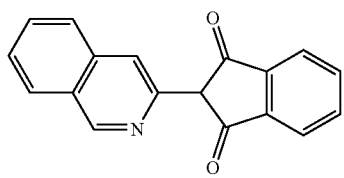

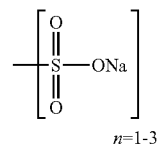

Solvent Green 5 (Tokyo Chemical Industry Co., Ltd.; having the structure shown below)

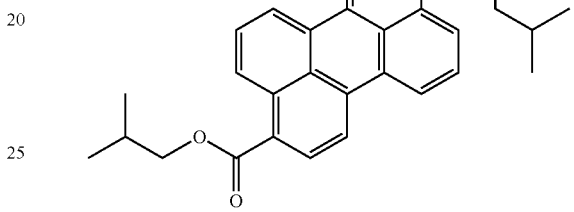

Indophenol blue (Tokyo Chemical Industry Co., Ltd.; having the structure shown below)

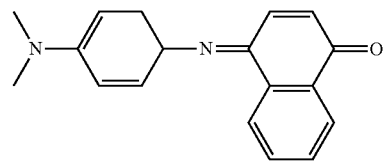

Phthalocyanine Green (Tokyo Chemical Industry Co., Ltd.; having the structure shown below)

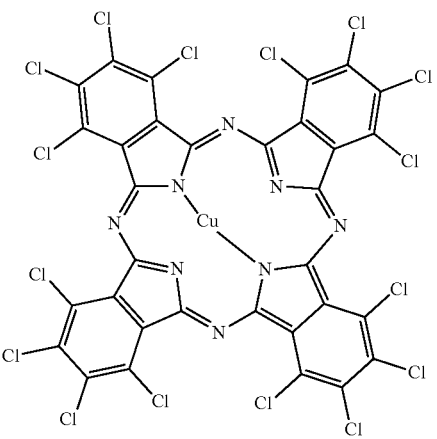

Phthalocyanine blue (Tokyo Chemical Industry Co., Ltd.; having the structure shown below)

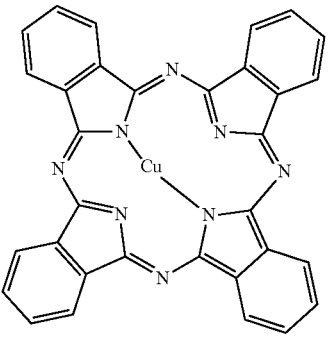

Solvent Blue 59 (Tokyo Chemical Industry Co., Ltd.; having the structure shown below)

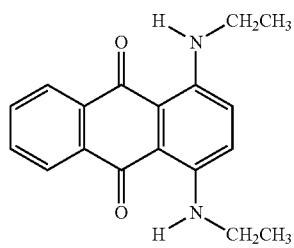 [SMILES: CCNc1ccc(NCC)c2c1C(=O)c1ccccc1C2=O]

The viscosities of the photocurable compositions of Examples 1 to 30 and 101 to 120, and Comparative Examples 1 to 4 and 101 to 107 were all in the range of 700 mPa·s to 1,000 mPa·s.

Examples 1 to 30 and Comparative Examples 1 to 4 (First embodiment; wavelength 405 nm)

<Transmittance (405 nm) of Diluted Solution (D2) of Each Colorant Compound and Each Photopolymerization Initiator>

For each colorant compound and each photopolymerization initiator used in the preparation of photocurable compositions, a diluted solution (D2) was prepared by diluting the compound with ethanol such that the content of the compound is 0.01% by mass.

The transmittance of each diluted solution (D2) was measured in the wavelength range of 300 nm to 750 nm using a UV-visible absorption spectrophotometer (EVOLUTION 220 manufactured by Thermo Scientific) with an optical path length of 0.5 cm. From the measurement results, the transmittance at 405 nm, which is the irradiation wavelength of the 3D printer, was read.

The results are shown in the "Transmittance (%) at 405 nm" column for each colorant compound and each photopolymerization initiator in Tables 1 to 3.

<Calculation of Sum of Values (A)>

For each of the colorant compounds in the prepared photocurable compositions, the value (A) was determined according to the above-described Formula (a) based on the transmittance (%) indicated in the "Transmittance (%) at 405 nm" column and the content, and the sum of the values (A) in each photocurable composition was calculated.

The results are shown in the "Sum of values (A)" column in Tables 1 to 3.

<Transmittance Measurement of Diluted Solution (D1) of Photocurable Composition (405 nm)>

The following transmittance measurement was performed on the prepared photocurable composition.

Diluted solution (D1) was prepared by diluting the prepared photocurable composition with ethanol such that the ethanol content was 99% by mass.

The transmittance of the diluted solution (D1) was measured in the wavelength range of 300 nm to 750 nm using a UV-visible absorption spectrophotometer (EVOLUTION 220 manufactured by Thermo Scientific) with an optical path length of 1 cm. From the measurement results, the transmittance at 405 nm, which is the irradiation wavelength of the 3D printer, was read.

The measurement results are shown in the "Transmittance (%) of diluted solution (D1) at 405 nm" column in Tables 1 to 3.

<Evaluation of Thickness Accuracy of Bottom Face Portion of Three-Dimensional Molded Product (405 nm)>

A three-dimensional molded product 10 shown in FIG. 1 was produced by optical molding according to the DLP method, using a DLP-type 3D printer (CARA PRINT 4.0 from Kulzer).

In the produced three-dimensional molded product 10, the thickness (design value) of the bottom face portion 12 is 1.500 mm.

The production of the three-dimensional molded product 10 was performed in which the side face portions 14 and 16 of the three-dimensional molded product 10 were sequentially formed from the upper side (a side located upstream in the gravity direction G) to the lower side (a side located downstream in the gravity direction G), and, lastly, the bottom face portion 12 was formed, in the same manner as that in the aforementioned example. Detailed operations were as described in the aforementioned example.

Each cured layer was formed by irradiating the photocurable composition with visible light having a wavelength of 405 nm at an irradiation dose of 10 mJ/cm$^2$. The thickness of each cured layer was set to 50 μm.

After the formation of all cured layers was completed to obtain the three-dimensional molded product 10, the entire three-dimensional molded product 10 formed was irradiated with ultraviolet light having a wavelength of 365 nm at an irradiation dose of 3 mJ/cm$^2$, to fully cure the three-dimensional molded product 10.

The thickness of the bottom face portion 12 of the three-dimensional molded product 10 after full curing was measured with a caliper (CD-P15S manufactured by Mitutoyo).

The measured thicknesses of the bottom face portion are shown in Tables 1 to 3 (in the "Thickness of bottom face portion at 405 nm" column).

When the measured thickness of the bottom face portion is within the range of 1.500 mm (design value) to 1.600 mm, judgment that the thickness accuracy is excellent can be made.

TABLE 1

| Components of photocurable composition | | Transmittance (%) of diluted solution (D2) at 405 nm | Comp. Ex. 1 | Comp. Ex. 2 | Comp. Ex. 3 | Comp. Ex. 4 | Ex. 1 | Ex. 2 |
|---|---|---|---|---|---|---|---|---|
| Colorant compound | Quinizarin | 57.3 | | | | 3 | 0.03 | |
| | Alizarin | 24.2 | | | | | | 0.02 |
| | Solvent Green 3 | 34.6 | | | | | | |
| | Sudan II | 6.7 | | | | | | |
| | Sudan III | 23.1 | | | | | | |
| | Sudan IV | 9.6 | | | | | | |
| | Solvent Orange 2 | 5.5 | | | | | | |
| | Solvent Yellow 2 | 0.5 | | | 0.1 | | | |
| | Solvent Yellow 11 | 10.2 | | | | | | |
| | Solvent Yellow 7 | 44.2 | | | | | | |
| | Basic Green 1 | 14.7 | | | | | | |
| | Acid Yellow 3 | 4.9 | | | | | | |
| | Solvent Green 5 | 45.7 | | | | | | |
| | Indophenol Blue | 72.3 | | | | | | |
| | Phthalocyanine Green | 23.5 | | | | | | |
| | Phthalocyanine Blue | 45.5 | | | | | | |
| | Solvent Blue 59 | 72.9 | | | | | | |
| Photopolymerizable component | ABE300 | — | 70 | | 70 | 70 | 70 | 70 |
| | UDA | — | 30 | | 30 | 30 | 30 | 30 |
| | SR540 | — | | 80 | | | | |
| | UDMA | — | | 20 | | | | |
| Photopolymerization initiator | TPO | 92.2 | 2 | 2 | 2 | 2 | 2 | 2 |
| | 819 | 87.5 | | | | | | |
| | Total amount | | 102 | 102 | 102.1 | 105 | 102.03 | 102.02 |
| | Sum of values (A) | | 0.00 | 0.00 | 20.00 | 5.24 | 0.05 | 0.08 |
| Transmittance (%) of diluted solution (D1) at 405 nm | | | 75.6 | 85.7 | 0.8 | 0.7 | 55.6 | 49.0 |
| Thickness (mm) of bottom face portion at 405 nm | | | 1.672 | 1.694 | Molding failure | Molding failure | 1.570 | 1.558 |

| Components of photocurable composition | | Transmittance (%) of diluted solution (D2) at 405 nm | Ex. 3 | Ex. 4 | Ex. 5 | Ex. 6 | Ex. 7 | Ex. 8 |
|---|---|---|---|---|---|---|---|---|
| Colorant compound | Quinizarin | 57.3 | | | | | | |
| | Alizarin | 24.2 | | | | | | |
| | Solvent Green 3 | 34.6 | 0.02 | | | | | |
| | Sudan II | 6.7 | | 0.02 | | | | |
| | Sudan III | 23.1 | | | 0.02 | 0.01 | | |
| | Sudan IV | 9.6 | | | | | 0.01 | |
| | Solvent Orange 2 | 5.5 | | | | | | 0.01 |
| | Solvent Yellow 2 | 0.5 | | | | | | |
| | Solvent Yellow 11 | 10.2 | | | | | | |
| | Solvent Yellow 7 | 44.2 | | | | | | |
| | Basic Green 1 | 14.7 | | | | | | |
| | Acid Yellow 3 | 4.9 | | | | | | |
| | Solvent Green 5 | 45.7 | | | | | | |
| | Indophenol Blue | 72.3 | | | | | | |
| | Phthalocyanine Green | 23.5 | | | | | | |
| | Phthalocyanine Blue | 45.5 | | | | | | |
| | Solvent Blue 59 | 72.9 | | | | | | |
| Photopolymerizable component | ABE300 | — | 70 | 70 | 70 | 70 | 70 | 70 |
| | UDA | — | 30 | 30 | 30 | 30 | 30 | 30 |
| | SR540 | — | | | | | | |
| | UDMA | — | | | | | | |
| Photopolymerization initiator | TPO | 92.2 | 2 | 2 | 2 | 2 | 2 | 2 |
| | 819 | 87.5 | | | | | | |
| | Total amount | | 102.02 | 102.02 | 102.02 | 102.01 | 102.01 | 102.01 |
| | Sum of values (A) | | 0.06 | 0.30 | 0.09 | 0.04 | 0.10 | 0.18 |
| Transmittance (%) of diluted solution (D1) at 405 nm | | | 51.3 | 42.5 | 41.4 | 64.8 | 54.0 | 53.5 |
| Thickness (mm) of bottom face portion at 405 nm | | | 1.567 | 1.533 | 1.531 | 1.591 | 1.571 | 1.569 |

Ex.: Example,
Comp. Ex.: Comparative Example

TABLE 2

| Components of photocurable composition | | Transmittance (%) of diluted solution (D2) at 405 nm | Ex. 9 | Ex. 10 | Ex. 11 | Ex. 12 | Ex. 13 | Ex. 14 |
|---|---|---|---|---|---|---|---|---|
| Colorant compound | Quinizarin | 57.3 | | | | | | |
| | Alizarin | 24.2 | | | | | | |
| | Solvent Green 3 | 34.6 | | | | | | |
| | Sudan II | 6.7 | | | | | | |
| | Sudan III | 23.1 | | | | | | |
| | Sudan IV | 9.6 | | | | | | |
| | Solvent Orange2 | 5.5 | | | | | | |
| | Solvent Yellow 2 | 0.5 | 0.01 | 0.015 | | | | |
| | Solvent Yellow 11 | 10.2 | | | 0.01 | | | |
| | Solvent Yellow 7 | 44.2 | | | | 0.02 | | |
| | Basic Green 1 | 14.7 | | | | | 0.01 | |
| | Acid Yellow 3 | 4.9 | | | | | | 0.01 |
| | Solvent Green 5 | 45.7 | | | | | | |
| | Indophenol Blue | 72.3 | | | | | | |
| | Phthalocyanine Green | 23.5 | | | | | | |
| | Phthalocyanine Blue | 45.5 | | | | | | |
| | Solvent Blue 59 | 72.9 | | | | | | |
| Photopolymerizable component | ABE300 | — | 70 | 70 | 70 | 70 | 70 | 70 |
| | UDA | — | 30 | 30 | 30 | 30 | 30 | 30 |
| | SR540 | — | | | | | | |
| | UDMA | — | | | | | | |
| Photopolymerization initiator | TPO | 92.2 | 2 | 2 | 2 | 2 | 2 | 2 |
| | 819 | 87.5 | | | | | | |
| | Total amount | | 102.01 | 102.015 | 102.01 | 102.02 | 102.01 | 102.01 |
| | Sum of values (A) | | 2.00 | 3.00 | 0.10 | 0.05 | 0.07 | 0.20 |
| | Transmittance (%) of diluted solution (D1) at 405 nm | | 18.7 | 3.8 | 46.1 | 60.7 | 59.4 | 57.1 |
| | Thickness (mm) of bottom face portion at 405 nm | | 1.504 | 1.501 | 1.546 | 1.581 | 1.586 | 1.579 |

| Components of photocurable composition | | Transmittance (%) of diluted solution (D2) at 405 nm | Ex. 15 | Ex. 16 | Ex. 17 | Ex. 18 | Ex. 19 | Ex. 20 |
|---|---|---|---|---|---|---|---|---|
| Colorant compound | Quinizarin | 57.3 | | | | | | 0.01 |
| | Alizarin | 24.2 | | | | | | |
| | Solvent Green 3 | 34.6 | | | | | | |
| | Sudan II | 6.7 | | | | | | |
| | Sudan III | 23.1 | | | | | | |
| | Sudan IV | 9.6 | | | | | | |
| | Solvent Orange2 | 5.5 | | | | | | |
| | Solvent Yellow 2 | 0.5 | | | | | | |
| | Solvent Yellow 11 | 10.2 | | | | | | |
| | Solvent Yellow 7 | 44.2 | | | | | | |
| | Basic Green 1 | 14.7 | | | | | | |
| | Acid Yellow 3 | 4.9 | | | | | | |
| | Solvent Green 5 | 45.7 | 0.02 | | | | | |
| | Indophenol Blue | 72.3 | | 0.05 | | | | |
| | Phthalocyanine Green | 23.5 | | | 0.03 | | | |
| | Phthalocyanine Blue | 45.5 | | | | 0.05 | | |
| | Solvent Blue 59 | 72.9 | | | | | 0.1 | |
| Photopolymerizable component | ABE300 | — | 70 | 70 | 70 | 70 | 70 | 70 |
| | UDA | — | 30 | 30 | 30 | 30 | 30 | 30 |
| | SR540 | — | | | | | | |
| | UDMA | — | | | | | | |
| Photopolymerization initiator | TPO | 92.2 | 2 | 2 | 2 | 2 | 2 | |
| | 819 | 87.5 | | | | | | 2 |
| | Total amount | | 102.02 | 102.05 | 102.03 | 102.05 | 102.1 | 102.01 |
| | Sum of values (A) | | 0.04 | 0.07 | 0.13 | 0.11 | 0.14 | 0.02 |
| | Transmittance (%) of diluted solution (D1) at 405 nm | | 49.5 | 53.8 | 56.9 | 60.3 | 59.0 | 27.2 |
| | Thickness (mm) of bottom face portion at 405 nm | | 1.561 | 1.575 | 1.580 | 1.587 | 1.588 | 1.516 |

Ex.: Example,
Comp. Ex.: Comparative Example

TABLE 3

| Components of photocurable composition | | Transmittance (%) of diluted solution (D2) at 405 nm | Ex. 21 | Ex. 22 | Ex. 23 | Ex. 24 | Ex. 25 |
|---|---|---|---|---|---|---|---|
| Colorant compound | Quinizarin | 57.3 | | | | | |
| | Alizarin | 24.2 | | | | | |
| | Solvent Green 3 | 34.6 | | | | 0.02 | |
| | Sudan II | 6.7 | | | | | |
| | Sudan III | 23.1 | 0.01 | | | | |
| | Sudan IV | 9.6 | | | | | 0.02 |
| | Solvent Orange2 | 5.5 | | | — | | |
| | Solvent Yellow 2 | 0.5 | | 0.01 | | | |
| | Solvent Yellow 11 | 10.2 | | | | | |
| | Solvent Yellow 7 | 44.2 | | | | | |
| | Basic Green 1 | 14.7 | | | | | |
| | Acid Yellow 3 | 4.9 | | | | | |
| | Solvent Green 5 | 45.7 | | | | | |
| | Indophenol Blue | 72.3 | | | | | |
| | Phthalocyanine Green | 23.5 | | | | | |
| | Phthalocyanine Blue | 45.5 | | | | | |
| | Solvent Blue 59 | 72.9 | | | 0.02 | | |
| Photopolymerizable component | ABE300 | — | 70 | 70 | 70 | | |
| | UDA | — | 30 | 30 | 30 | | |
| | SR540 | — | | | | 80 | 80 |
| | UDMA | — | | | | 20 | 20 |
| Photopolymerization initiator | TPO | 92.2 | | | | 2 | 2 |
| | 819 | 87.5 | 2 | 2 | 2 | | |
| | Total amount | | 102.01 | 102.01 | 102.02 | 102.02 | 102.02 |
| | Sum of values (A) | | 0.04 | 2.00 | 0.03 | 0.06 | 0.21 |
| | Transmittance (%) of diluted solution (D1) at 405 nm | | 22.7 | 13.3 | 27.2 | 52.6 | 38.3 |
| | Thickness (mm) of bottom face portion at 405 nm | | 1.510 | 1.504 | 1.518 | 1.564 | 1.527 |

| Components of photocurable composition | | Transmittance (%) of diluted solution (D2) at 405 nm | Ex. 26 | Ex. 27 | Ex. 28 | Ex. 29 | Ex. 30 |
|---|---|---|---|---|---|---|---|
| Colorant compound | Quinizarin | 57.3 | | 0.01 | | | |
| | Alizarin | 24.2 | | | | | |
| | Solvent Green 3 | 34.6 | | | | | |
| | Sudan II | 6.7 | | | | | |
| | Sudan III | 23.1 | | | 0.01 | | |
| | Sudan IV | 9.6 | | | | | |
| | Solvent Orange2 | 5.5 | | | | | |
| | Solvent Yellow 2 | 0.5 | 0.01 | | | 0.01 | |
| | Solvent Yellow 11 | 10.2 | | | | | |
| | Solvent Yellow 7 | 44.2 | | | | | |
| | Basic Green 1 | 14.7 | | | | | |
| | Acid Yellow 3 | 4.9 | | | | | |
| | Solvent Green 5 | 45.7 | | | | | |
| | Indophenol Blue | 72.3 | | | | | |
| | Phthalocyanine Green | 23.5 | | | | | |
| | Phthalocyanine Blue | 45.5 | | | | | |
| | Solvent Blue 59 | 72.9 | | | | | 0.02 |
| Photopolymerizable component | ABE300 | — | | | | | |
| | UDA | — | | | | | |
| | SR540 | — | 80 | 80 | 80 | 80 | 80 |
| | UDMA | — | 20 | 20 | 20 | 20 | 20 |
| Photopolymerization initiator | TPO | 92.2 | 2 | | | | |
| | 819 | 87.5 | | 2 | 2 | 2 | 2 |
| | Total amount | | 102.01 | 102.01 | 102.01 | 102.01 | 102.02 |
| | Sum of values (A) | | 2.00 | 0.02 | 0.04 | 2.00 | 0.03 |
| | Transmittance (%) of diluted solution (D1) at 405 nm | | 20.0 | 31.3 | 24.8 | 17.6 | 29.2 |
| | Thickness (mm) of bottom face portion at 405 nm | | 1.509 | 1.520 | 1.511 | 1.503 | 1.522 |

Ex.: Example,
Comp. Ex.: Comparative Example

As shown in Tables 1 to 3, the thickness of the bottom face portion of the three-dimensional molded product was within the range of 1.500 mm (design value) to 1.600 mm in Examples 1 to 30, in which the diluted solution (D1) satisfied Condition (1) (transmittance at a wavelength of 405 nm is from 1.0% to 70.0%), thus exhibiting an excellent thickness accuracy.

In contrast, in Comparative Examples 1 and 2, in which the transmittance of the diluted solution (D1) was more than 70.0% at a wavelength of 405 nm, the thickness of the bottom face portion of the three-dimensional molded product was more than 1.600 mm, thus exhibiting an inferior thickness accuracy (exhibiting an excessively large thickness).

In Comparative Examples 3 and 4, in which the transmittance of the diluted solution (D1) was less than 1.0% at a wavelength of 405 nm, curing was insufficient, and a molding defect occurred.

Examples 101 to 120 and Comparative Examples 101 to 107 (Second embodiment; wavelength 385 nm)

<Transmittance (385 nm) of Diluted Solution (D2) of Each Colorant Compound and Each Photopolymerization Initiator>

For each colorant compound and each photopolymerization initiator used in the preparation of photocurable compositions, a diluted solution (D2) was prepared by diluting the compound with ethanol such that the content of the compound is 0.01% by mass.

The transmittance of each diluted solution (D2) was measured in the wavelength range of 300 nm to 750 nm using a UV-visible absorption spectrophotometer (EVOLUTION 220 manufactured by Thermo Scientific) with an optical path length of 0.5 cm. From the measurement results, the transmittance at 385 nm, which is the irradiation wavelength of the 3D printer, was read.

The results are shown in the "Transmittance (%) at 385 nm" column for each colorant compound and each photopolymerization initiator in Table 4 and Table 5.

<Calculation of Sum of Values (B)>

For each of the colorant compounds in the prepared photocurable compositions, the value (B) was determined according to the above-described Formula (b) based on the transmittance (%) indicated in the "Transmittance (%) at 385 nm" column, and the sum of the values (B) in each photocurable composition was calculated.

The results are shown in the "Sum of values (B)" column in Table 4 and Table 5.

<Transmittance Measurement of Diluted Solution (D1) of Photocurable Composition (385 nm)>

The following transmittance measurement was performed on the prepared photocurable composition.

Diluted solution (D1) was prepared by diluting the prepared photocurable composition with ethanol such that the ethanol content was 99% by mass.

The transmittance of the diluted solution (D1) was measured in the wavelength range of 300 nm to 750 nm using a UV-visible absorption spectrophotometer (EVOLUTION 220 manufactured by Thermo Scientific) with an optical path length of 1 cm. From the measurement results, the transmittance at 385 nm, which is the irradiation wavelength of the 3D printer, was read.

The results are shown in the "Transmittance (%) of diluted solution (D1) at 385 nm" column in Table 4 and Table 5.

<Evaluation of Thickness Accuracy of Bottom Face Portion of Three-Dimensional Molded Product (385 nm)>

The same operations as those in "Evaluation of Thickness Accuracy of Bottom Face Portion of Three-dimensional Molded Product (405 nm)" in Example 1 were performed to carry out the evaluation of the thickness accuracy of the bottom face portion of the three-dimensional molded product (385 nm), except for the following points.

A DLP-type 3D printer (MAX UV from Asiga) was used in place of a DLP-type 3D printer (CARA PRINT 4.0 from Kulzer).

The operation of forming each cured layer by irradiating the photocurable composition with visible light having a wavelength of 405 nm at an irradiation dose of 10 mJ/cm² was replaced by an operation of forming each cured layer by irradiating the photocurable composition with visible light having a wavelength of 385 nm at an irradiation dose of 7 mJ/cm².

The measured thickness of the bottom face portion is shown in the "Thickness of Bottom Face Portion at 385 nm" column in Table 4 and Table 5.

The criteria of judgement for thickness accuracy are the same as the criteria of judgement for thickness accuracy in the "Evaluation of Thickness Accuracy of Bottom Face Portion of Three-dimensional Molded Product (405 nm)".

TABLE 4

| Components | | Transmittance (%) of diluted solution (D2) at 385 nm | Comp. Ex. 101 | Comp. Ex. 102 | Comp. Ex. 103 | Comp. Ex. 104 | Comp. Ex. 105 | Comp. Ex. 106 | Comp. Ex. 107 |
|---|---|---|---|---|---|---|---|---|---|
| Colorant compound | Quinizarin | 79.1 | | | | | | | 3 |
| | Solvent Green 3 | 39.5 | | | | | | | |
| | Sudan II | 12.7 | | | | | | | |
| | Sudan III | 25.7 | | | | | | | |
| | Sudan IV | 9.4 | | | | | | | |
| | Solvent Orange 2 | 10.5 | | | | | | | |
| | Solvent Yellow 2 | 0.5 | | | | | | 0.1 | |
| | Solvent Yellow 11 | 8.6 | | | | | | | |
| | Solvent Yellow 7 | 5.2 | | | | | | | |
| | Solvent Green 5 | 71.7 | | | | | | | |
| | Indophenol blue | 65.5 | | | | | | | |
| | Phthalocyanine Green | 21.2 | | | | | | | |
| | Phthalocyanine Blue | 23.5 | | | | | | | |
| | Solvent Blue 59 | 59.9 | | | | | | | |

TABLE 4-continued

| | | | | | | | | | |
|---|---|---|---|---|---|---|---|---|---|
| Photopolymerizable component | ABE300 | — | 70 | | 70 | 70 | 70 | 70 | 70 |
| | EB4858 | — | 30 | | 30 | 30 | 30 | 30 | 30 |
| | SR540 | — | | 80 | | | | | |
| | UDMA | — | | 20 | | | | | |
| Photopolymerization initiator | TPO | 85.5 | 0.5 | 0.5 | 1 | | | 0.5 | 0.5 |
| | 184 | 95.8 | | | | 5 | | | |
| | MBF | 96.2 | | | | | 5 | | |
| | Total amount | | 100.5 | 100.5 | 101 | 105 | 105 | 100.6 | 103.5 |
| | Sum of values (B) | | 0.00 | 0.00 | 0.00 | 0.00 | 0.00 | 20.00 | 3.79 |
| Transmittance (%) of diluted solution (D1) at 385 nm | | | 83.2 | 84.0 | 86.5 | 93.5 | 91.5 | 0.8 | 0.4 |
| Thickness (mm) of bottom face portion at 385 nm | | | 1.802 | 1.821 | 1.674 | 2.289 | 1.996 | Molding failure | Molding failure |

| | Components | Transmittance (%) of diluted solution (D2) at 385 nm | Ex. 101 | Ex. 102 | Ex. 103 | Ex. 104 | Ex. 105 | Ex. 106 |
|---|---|---|---|---|---|---|---|---|
| Colorant compound | Quinizarin | 79.1 | 0.05 | | | | | |
| | Solvent Green 3 | 39.5 | | 0.03 | | | | |
| | Sudan II | 12.7 | | | 0.02 | | | |
| | Sudan III | 25.7 | | | | 0.02 | | |
| | Sudan IV | 9.4 | | | | | 0.02 | |
| | Solvent Orange 2 | 10.5 | | | | | | 0.02 |
| | Solvent Yellow 2 | 0.5 | | | | | | |
| | Solvent Yellow 11 | 8.6 | | | | | | |
| | Solvent Yellow 7 | 5.2 | | | | | | |
| | Solvent Green 5 | 71.7 | | | | | | |
| | Indophenol blue | 65.5 | | | | | | |
| | Phthalocyanine Green | 21.2 | | | | | | |
| | Phthalocyanine Blue | 23.5 | | | | | | |
| | Solvent Blue 59 | 59.9 | | | | | | |
| Photopolymerizable component | ABE300 | — | 70 | 70 | 70 | 70 | 70 | 70 |
| | EB4858 | — | 30 | 30 | 30 | 30 | 30 | 30 |
| | SR540 | — | | | | | | |
| | UDMA | — | | | | | | |
| Photopolymerization initiator | TPO | 85.5 | 0.5 | 0.5 | 0.5 | 0.5 | 0.5 | 0.5 |
| | 184 | 95.8 | | | | | | |
| | MBF | 96.2 | | | | | | |
| | Total amount | | 100.55 | 100.53 | 100.52 | 100.52 | 100.52 | 100.52 |
| | Sum of values (B) | | 0.06 | 0.08 | 0.16 | 0.08 | 0.21 | 0.19 |
| Transmittance (%) of diluted solution (D1) at 385 nm | | | 60.1 | 54.7 | 46.1 | 44.8 | 40.1 | 40.5 |
| Thickness (mm) of bottom face portion at 385 nm | | | 1.581 | 1.572 | 1.544 | 1.541 | 1.536 | 1.534 |

Ex.: Example,
Comp. Ex.: Comparative Example

TABLE 5

| | Components | Transmittance (%) of diluted solution (D2) at 385 nm | Ex. 107 | Ex. 108 | Ex. 109 | Ex. 110 | Ex. 111 | Ex. 112 | Ex. 113 |
|---|---|---|---|---|---|---|---|---|---|
| Colorant compound | Quinizarin | 79.1 | | | | | | | |
| | Solvent Green 3 | 39.5 | | | | | | | |
| | Sudan II | 12.7 | | | | | | | |
| | Sudan III | 25.7 | | | | | | | |
| | Sudan IV | 9.4 | | | | | | | |
| | Solvent Orange 2 | 10.5 | | | | | | | |
| | Solvent Yellow 2 | 0.5 | 0.01 | 0.015 | | | | | |
| | Solvent Yellow 11 | 8.6 | | | 0.02 | | | | |
| | Solvent Yellow 7 | 5.2 | | | | 0.02 | | | |
| | Solvent Green 5 | 71.7 | | | | | 0.05 | | |
| | Indophenol Blue | 65.5 | | | | | | 0.05 | |
| | Phthalocyanine Green | 21.2 | | | | | | | 0.02 |
| | Phthalocyanine Blue | 23.5 | | | | | | | |
| | Solvent Blue 59 | 59.9 | | | | | | | |
| Photopolymerizable component | ABE300 | — | 70 | 70 | 70 | 70 | 70 | 70 | 70 |
| | EB4858 | — | 30 | 30 | 30 | 30 | 30 | 30 | 30 |
| | SR540 | — | | | | | | | |
| | UDMA | — | | | | | | | |

TABLE 5-continued

| | | Transmittance (%) of diluted solution (D2) at 385 nm | | | | | | | |
|---|---|---|---|---|---|---|---|---|---|
| Photopolymerization initiator | TPO | 85.5 | 0.5 | 0.5 | 0.5 | 0.5 | 0.5 | 0.5 | 0.5 |
| | 184 | 95.8 | | | | | | | |
| | MBF | 96.2 | | | | | | | |
| | Total amount | | 100.51 | 100.515 | 100.52 | 100.52 | 100.55 | 100.55 | 100.52 |
| | Sum of values (B) | | 2.00 | 3.00 | 0.23 | 0.38 | 0.07 | 0.08 | 0.09 |
| | Transmittance (%) of diluted solution (D1) at 385 nm | | 23.2 | 8.6 | 44.6 | 35.1 | 61.6 | 58.3 | 39.8 |
| | Thickness (mm) of bottom face portion at 385 nm | | 1.511 | 1.504 | 1.544 | 1.524 | 1.581 | 1.577 | 1.530 |

| Components | | Transmittance (%) of diluted solution (D2) at 385 nm | Ex. 114 | Ex. 115 | Ex. 116 | Ex. 117 | Ex. 118 | Ex. 119 | Ex. 120 |
|---|---|---|---|---|---|---|---|---|---|
| Colorant compound | Quinizarin | 79.1 | | | | | | | |
| | Solvent Green 3 | 39.5 | | | | | | | |
| | Sudan II | 12.7 | | | | | | | |
| | Sudan III | 25.7 | | | | | | | |
| | Sudan IV | 9.4 | | | | | | | |
| | Solvent Orange 2 | 10.5 | | | | | | | |
| | Solvent Yellow 2 | 0.5 | | | 0.01 | 0.01 | 0.01 | 0.01 | 0.01 |
| | Solvent Yellow 11 | 8.6 | | | | | | | |
| | Solvent Yellow 7 | 5.2 | | | | | | | |
| | Solvent Green 5 | 71.7 | | | | | | | |
| | Indophenol Blue | 65.5 | | | | | | | |
| | Phthalocyanine Green | 21.2 | | | | | | | |
| | Phthalocyanine Blue | 23.5 | 0.02 | | | | | | |
| | Solvent Blue 59 | 59.9 | | 0.05 | | | | | |
| Photopolymerizable component | ABE300 | — | 70 | 70 | | 70 | | 70 | |
| | EB4858 | — | 30 | 30 | | 30 | | 30 | |
| | SR540 | — | | | 80 | | 80 | | 80 |
| | UDMA | — | | | 20 | | 20 | | 20 |
| Photopolymerization initiator | TPO | 85.5 | 0.5 | 0.5 | 0.5 | | | | |
| | 184 | 95.8 | | | | 5 | 5 | | |
| | MBF | 96.2 | | | | | | 5 | 5 |
| | Total amount | | 100.52 | 100.55 | 100.51 | 105.01 | 105.01 | 105.01 | 105.01 |
| | Sum of values (B) | | 0.09 | 0.08 | 2.00 | 2.00 | 2.00 | 2.00 | 2.00 |
| | Transmittance (%) of diluted solution (D1) at 385 nm | | 42.3 | 51.3 | 24.1 | 53.3 | 54.4 | 49.9 | 51.8 |
| | Thickness (mm) of bottom face portion at 385 nm | | 1.533 | 1.561 | 1.512 | 1.566 | 1.564 | 1.561 | 1.563 |

Ex.: Example,
Comp. Ex.: Comparative Example

As shown in Table 4 and Table 5, the thickness of the bottom face portion of the three-dimensional molded product was within the range of 1.500 mm (design value) to 1.600 mm in Examples 101 to 120, in which the diluted solution (D1) satisfied Condition (2) (transmittance at 385 nm is from 1.0% to 70.0%), thus exhibiting an excellent thickness accuracy.

In contrast, in Comparative Examples 101 to 105, in which the transmittance of the diluted solution (D1) was more than 70.0% at a wavelength of 385 nm, the thickness of the bottom face portion of the three-dimensional molded product was more than 1.600 mm, thus exhibiting an inferior thickness accuracy.

In Comparative Examples 106 and 107, in which the transmittance of the diluted solution (D1) was less than 1.0% at a wavelength of 385 nm, curing was insufficient, and a molding defect occurred.

The disclosure of Japanese Patent Application No. 2020-008136, filed on Jan. 22, 2020, is incorporated herein by reference in its entirety.

All documents, patent applications, and technical standards described herein are incorporated herein by reference to the same extent as if each dididvidual document, patent application, or technical standard were specifically and individually indicated to be incorporated by reference.

The invention claimed is:

1. A photocurable composition comprising a photopolymerizable component and a photopolymerization initiator,
wherein a diluted solution (D1), which is prepared by diluting the photocurable composition with ethanol such that a content of ethanol is 99% by mass, satisfies the following Condition (X):
Condition (X): A transmittance at at least one wavelength within a wavelength range of from 365 nm to 405 nm, measured at an optical path length of 1 cm, is from 1.0% to 70.0%.

2. The photocurable composition according to claim 1, wherein the diluted solution (D1) satisfies at least one of the following Condition (1) or Condition (2):
Condition (1): A transmittance at a wavelength of 405 nm, measured at an optical path length of 1 cm, is from 1.0% to 70.0%, or
Condition (2): A transmittance at a wavelength of 385 nm, measured at an optical path length of 1 cm, is from 1.0% to 70.0%.

3. The photocurable composition according to claim 2, further comprising a colorant compound.

4. The photocurable composition according to claim 3, wherein:
when the diluted solution (D1) satisfies the Condition (1), a sum of values (A) defined in the following Formula (a) for respective colorant compounds contained in the photocurable composition is from 0.01 to 3.00, and when the diluted solution (D1) satisfies the Condition (2), a sum of values (B) defined in the following formula (b) for respective colorant compounds contained in the photocurable composition is from 0.01 to 3.00, $$\text{value}(A) = (x_1/y_1) \times 100 \quad \text{Formula (a)}$$

$$\text{value}(B) = (x_2/y_2) \times 100 \quad \text{Formula (b)}$$

wherein, in Formula (a),
- $x_1$ represents a content of a colorant compound in parts by mass with respect to 100 parts by mass of the photopolymerizable component contained in the photocurable composition, and
- $y_1$ represents a transmittance (%) at a wavelength of 405 nm measured at an optical path length of 0.5 cm for a diluted solution (D2) obtained by dilution with ethanol such that a content of the colorant compound is 0.01% by mass, and wherein, in Formula (b),
- $x_2$ represents a content of the colorant compound in parts by mass with respect to 100 parts by mass of the photopolymerizable component contained in the photocurable composition, and
- $y_2$ represents a transmittance (%) at a wavelength of 385 nm measured at an optical path length of 0.5 cm for the diluted solution (D2) obtained by dilution with ethanol such that the content of the colorant compound is 0.01% by mass.

5. The photocurable composition according to claim 3, wherein:
when the diluted solution (D1) satisfies the Condition (1), each colorant compound contained in the photocurable composition satisfies the following Condition (1-1), and
when the diluted solution (D1) satisfies the Condition (2), each colorant compound contained in the photocurable composition satisfies the following Condition (2-1),
Condition (1-1): A transmittance at a wavelength of 405 nm, measured at an optical path length of 0.5 cm for a diluted solution (D2) obtained by dilution with ethanol such that a content of a colorant compound is 0.01% by mass, is from 0.1% to 80.0%,
Condition (2-1): A transmittance at a wavelength of 385 nm, measured at an optical path length of 0.5 cm for the diluted solution (D2) obtained by dilution with ethanol such that the content of the colorant compound is 0.01% by mass, is from 0.1% to 80.0%.

6. The photocurable composition according to claim 3, wherein the colorant compound comprises at least one of a dye or a pigment.

7. The photocurable composition according to claim 1, wherein the photopolymerizable component comprises a (meth)acrylic monomer.

8. The photocurable composition according to claim 7, wherein:
the (meth)acrylic monomer comprises at least one of a monofunctional (meth)acrylic monomer or a bifunctional (meth)acrylic monomer, and
a total amount of the bifunctional (meth)acrylic monomer and the monofunctional (meth)acrylic monomer with respect to a total amount of the (meth)acrylic monomer is 90% by mass or more.

9. The photocurable composition according to claim 7, wherein the (meth)acrylic monomer comprises a bifunctional (meth)acrylic monomer.

10. The photocurable composition according to claim 1, wherein the photocurable composition does not comprise any inorganic filler, or, in a case in which the photocurable composition comprises an inorganic filler, a content of the inorganic filler with respect to a total amount of the photocurable composition is 10% by mass or less.

11. The photocurable composition according to claim 1, wherein a viscosity, measured by an E-type viscometer under conditions of 25° C. and 50 rpm, is from 5 mPa·s to 6,000 mPa·s.

12. The photocurable composition according to claim 1, which is a photocurable composition for optical molding.

13. The photocurable composition according to claim 1, which is used for producing dental products by optical molding.

14. A three-dimensional molded product that is a cured product of the photocurable composition according to claim 1.

15. The three-dimensional molded product according to claim 14, comprising at least one of a recess portion or a space.

16. A dental product comprising the three-dimensional molded product according to claim 14.

* * * * *